United States Patent [19]

Holroyd et al.

[11] 4,197,329
[45] Apr. 8, 1980

[54] BLOOD FILMING PROCESS

[75] Inventors: Joseph A. Holroyd, Nabnasset; Robert K. Mitchiner, Framingham, both of Mass.

[73] Assignee: Dynatech Corporation, Burlington, Mass.

[21] Appl. No.: 556,581

[22] Filed: Mar. 10, 1975

[51] Int. Cl.² .................................................. B05C 11/08
[52] U.S. Cl. ............................................. 427/2; 118/52
[58] Field of Search ..................... 427/2, 240; 118/52

[56] References Cited

U.S. PATENT DOCUMENTS

| | | | |
|---|---|---|---|
| 3,130,099 | 4/1964 | Homburger | 118/52 |
| 3,577,267 | 5/1971 | Preston et al. | 427/2 |
| 3,705,048 | 12/1972 | Staunton | 427/2 |
| 3,870,014 | 3/1975 | Buck | 118/501 |
| 3,906,890 | 9/1975 | Amos et al. | 118/52 |

Primary Examiner—Sam Silverberg
Attorney, Agent, or Firm—Robert A. Cesari; John F. McKenna; Andrew F. Kehoe

[57] ABSTRACT

An improved liquid-filming apparatus of the type which utilizes centrifugal action to distribute blood on a specimen-display surface, i.e. on a conventional laboratory slide, and which utilizes a waste-collecting means about the perimeter of the slide display surface. The invention is based on the discovery that the display surface is advantageously related to the surrounding structure in such a way that blood does not disintegrate into minute droplets upon leaving the slide surface and before it can be immobilized in the collecting means. By providing a transitional blood-receiving surface immediately adjacent the supply surface, applicant has avoided the problem of such disintegration.

2 Claims, 6 Drawing Figures

BLOOD FILMING PROCESS

BACKGROUND OF THE INVENTION

Centrifugal devices for distributing blood specimens over display surfaces are well known. In the most common form, they include a means for positioning and holding a microscope slide on which a blood sample is placed. The slide is then spun about at high speed to achieve the desired placement of the blood.

This invention relates to a process, and apparatus useful therein, for distributing blood on, say, a glass slide for subsequent inspection with a microscope. Such distribution is often referred to as "filming " by those working in medical laboratories.

There are a number of problems associated with the distribution of a blood sample on a glass slide. Perhaps the most obvious problem is that of obtaining an even distribution over the entire slide. The usual manual method consists of placing a drop of blood on the slide and then using a second slide to smear the blood along the slide. This technique usually results in poor lateral distribution, and the excessively narrow smear along the slide usually consists of excessively thick and ultra-thin areas. To avoid such problems, centrifugal equipment was introduced which utilized centrifugal force to spread blood along the length of a spinning slide and utilized the acceleration of the slide to achieve a lateral distribution of the blood.

The centrifugal procedure is a substantial advance in the art, especially as practiced with apparatus disclosed in commonly-owned and copending U.S. Pat. application Ser. No. 469,099 filed May 13, 1974 by Barger and Holroyd. In that application, apparatus is described wherein a waste-blood receiving means rotates with the blood-specimen bearing slide and collects specimen waste which is thrown off the slide. This apparatus is a very substantial advance over the art; it markedly reduces the potential for air contamination by any disease-bearing airborne waste resulting from operation of centrifugal blood filmers. Nevertheless, when filter paper is taped inside the top cover of a device of the type described in Ser. No. 469,099, it is usually still possible to detect several pin-point sized deposits of blood indicating some undesirable air transport of specimen material. It should be emphasized that the quantity of such material is magnitudes below that experienced with prior art blood filmers; nevertheless, it is desirable to reduce this so-called "aerosol" to as close to zero as can be accomplished. Various changes in the operating conditions and design parameters did not yield a solution to the problem: the "pin-point" contamination persisted.

It was work directed towards finding a means to achieve the reduction of such contamination which was undertaken by the instant inventors. It is the results of such work that are the subject of the instant disclosure.

SUMMARY OF THE INVENTION

It is a principal object of the invention to provide an improved blood-filmer of the centrifugal type, a filmer which may be operated with markedly-reduced formation of aerosol by specimen waste.

A further object of the invention is to provide an improved means for centrifugal distributing of physiological specimens on a display surface.

Another object of the invention is to provide means for retaining a slide in a centrifuge in such a manner that specimen waste is not dispersed excessively on leaving the slide surface.

Other objects of the invention will be obvious to those skilled in the art on their reading of this disclosure.

The above objects have been substantially achieved by construction of a novel structure for holding a specimen display surface and by controlling the path of specimen waste as it leaves the slide. This control is provided by using a waste-receiving transport surface i.e., a smooth deck along which specimen waste moves towards a specimen-waste receiving means.

The invention partially results from the discovery that prior-art apparatus had one or two structural features which contributed to dispersal of blood waste during the centrifuging process. The first of these was the use of slide retaining posts which, to be capable of retaining the slide during the quick acceleration and deceleration steps without the slide jumping out of position, were excessively large. For example, such posts would be as high, higher, or almost as high as the display surface on the slide. It was found that waste blood leaving the surface would impinge on the structure of the posts and be broken down and dispersed as it left the slide surface. Moreover, the waste-capturing device was spaced too far from the slide surface. This spacing was partly assignable to the diameter of the retaining posts. In any event, the spacing was sufficient to allow the blood to fragment after it left the slide surface and before it reached a waste-receiving means mounted thereabout. By "fragment" is meant the phenomena wherein the liquid blood sample, which tends to form in a relatively large, stringy or fibrous structures, as it leaves the slide surfaces under the impetus of centrifugal force, disintegrates to form a large number of blood fragments including many which are extremely small. In this application the "structural integrity" of waste blood defines the condition wherein said stringy or fibrous structures are not broken down to form aerosols or minute droplets.

Once discovering these phenomena relating to fragmentation of waste blood, the inventors constructed a centrifuge which has the following features.

1. The slide is not separated from rotating waste-receiving structure by retaining posts; rather, it is retained by the continuous-perimeter of a slide-restraining well.
2. The restraining well is defined by a perimeter inside of which the specimen-bearing surface is placed and outside of which is a deck portion which acts as a surface for receiving blood waste and guiding and transporting the waste with no substantial degradation into a waste-receiving means.
3. The above-identified structural features advantageously bear the following relationship to the plane of the display surface:

The plane of the receiving deck should be, roughly, in planar registration with the display surface of the slide. If properly positioned from the slide, i.e. no more than about 0.025 inch from the slide, it can be as much as 0.005 inch above the slide or 0.005 inch below the slide.

ILLUSTRATIVE EMBODIMENT OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

The apparatus with which the invention may be used most satisfactorily is described in detail in FIGS. 1 through 4.

However, the subject matter of applicants' invention is particularly described in FIGS. 5 and 6. It should be realized that the apparatus described in FIGS. 1 through 4 is not the only apparatus that can be used in conjunction with the invention: it is generally useful with all centrifugal blood filming apparatus. For example, it would be easily utilized on apparatus which utilizes a round or square slide or wafers (as in semiconductor processing), although the apparatus of FIGS. 1 through 4 is particularly directed at improving the convenience of processing rectangular slides.

IN THE DRAWINGS

Figure 1:
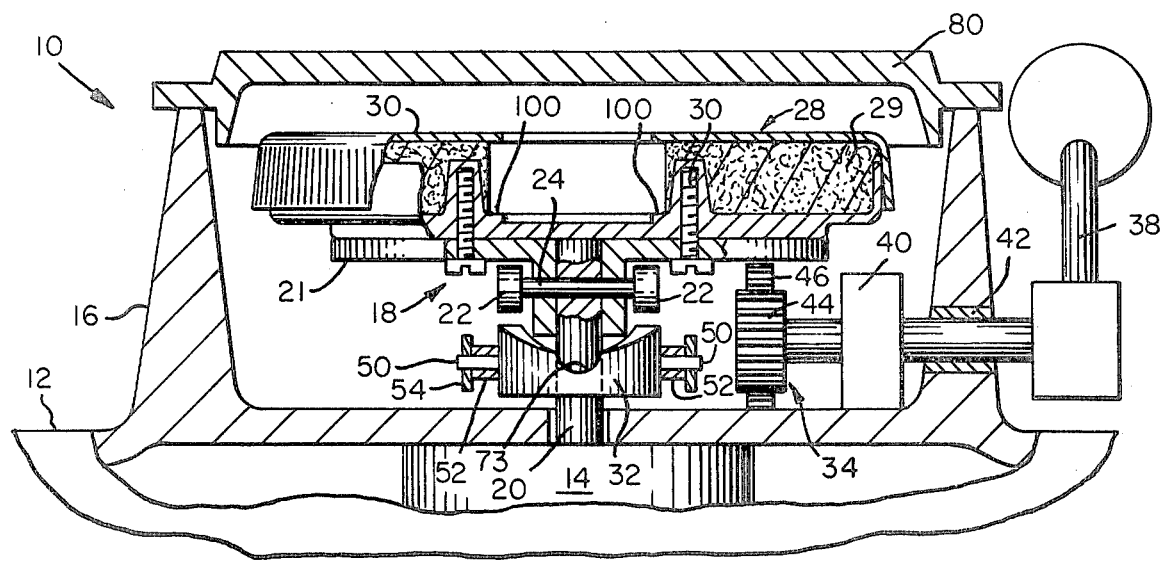
FIG. 1 is a side elevation of the apparatus of the invention with the slide positioning members disengaged as they would be during rotation of the slide.

Referring to FIG. 1, it is seen that blood filming apparatus 10 comprises a lower housing 12 enclosing motor 14 and an upper turret section 16 enclosing a slide-carrying assembly 18. Assembly 18 is adapted to be rotated on shaft 20 by motor 14.

Assembly 18 comprises a pair of cam follower rollers 22 which are fixed to carrier plate 21 by pin 24. Upon plate 21 is mounted a specimen waste-receiving means 28, attached to plate 21 by studs 30, means 28 being a disposable item is mounted top-most to facilitate replacement thereof.

Below slide-carrying assembly 18, and positioned about shaft 20 but having no connection thereto, is a cylindrical cam-bearing member 32. Member 32 may be seen more clearly in FIG. 3 and will be described more fully below with reference to FIG. 3.

Figure 2:
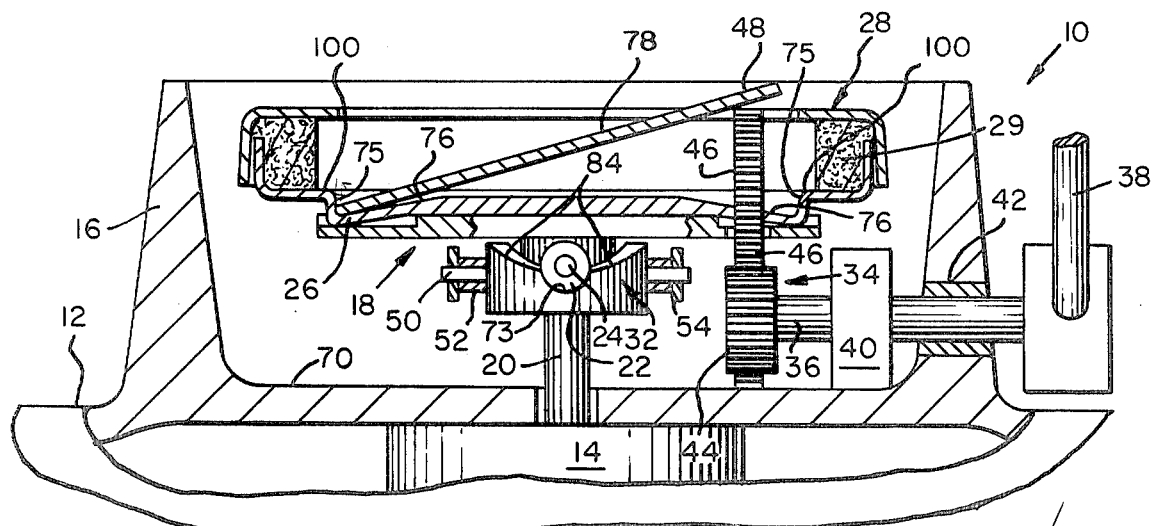
FIG. 2 is an elevation as shown in FIG. 1 except that the apparatus is shown with positioning members engaged, with the slide-holding assembly turned 90° because of said engagement, and with the slide tilting mechanism positioned to tilt the slide for easy removal.
Figure 4:
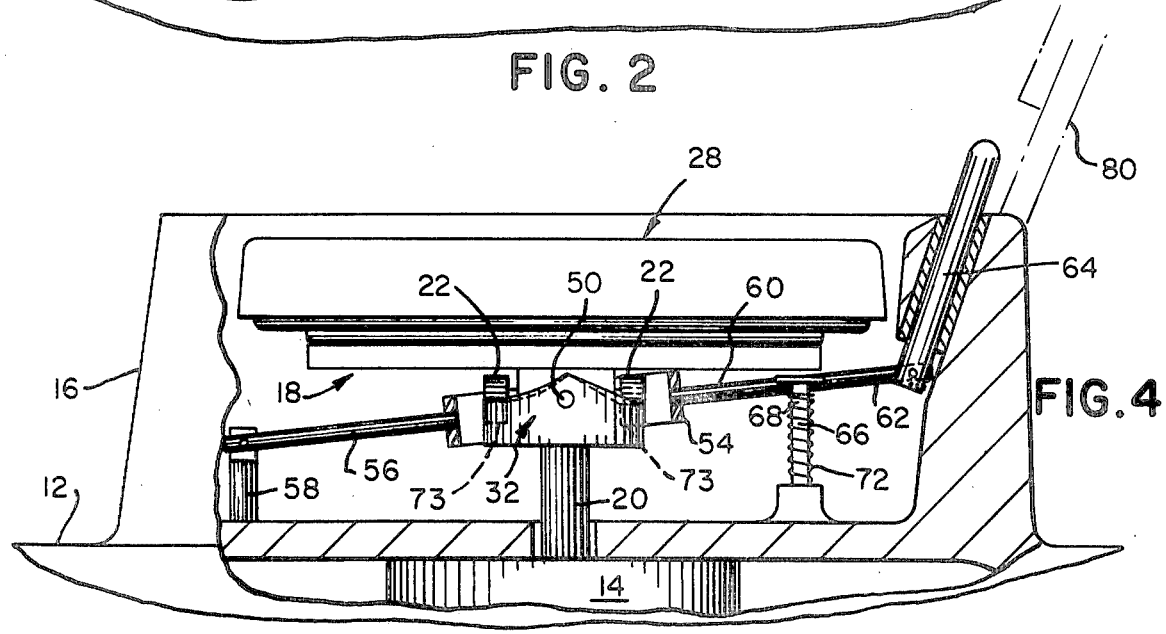
FIG. 4 is a schematic view of the apparatus shown in FIGS. 1 and 2 taken at a 90° angle thereto. It is particularly designed to show the handle-actuated operation of the cam positioning means.

FIG. 1 also illustrates a rack-and-gear assembly 34 which is operated via shaft 36 by lever arm 38. Shaft 36 is held by a bearing 40 and enters turret section 16 through another bearing 42. FIG. 2 illustrates how, when a slide 78 has stopped in proper position, rack 46 can be raised by gear 44 to engage end 48 of the slide and lift it clear of waste-receiving means 28, thereby facilitating the handling by the operator.

Figure 3:
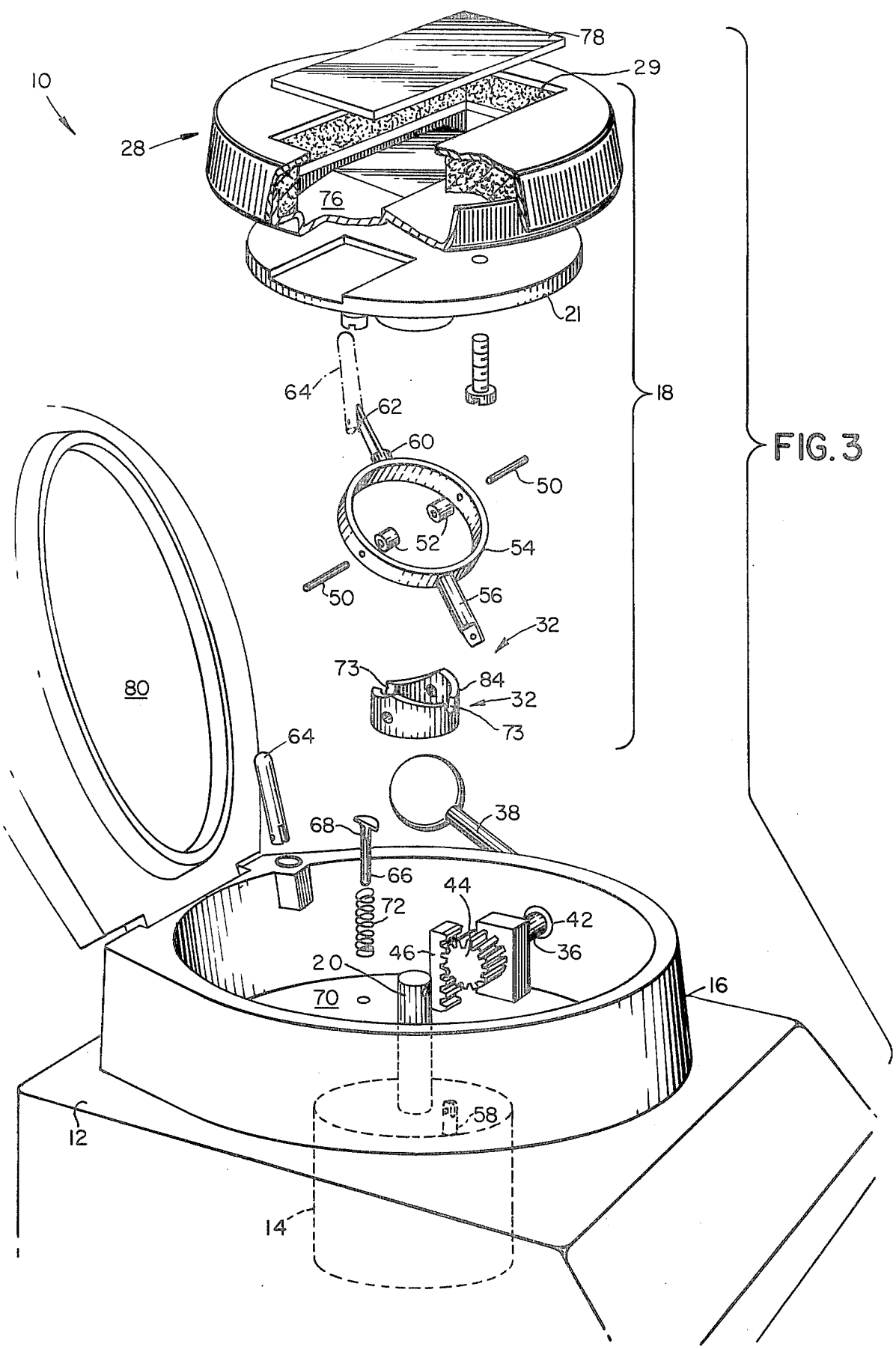
FIG. 3 is an exploded view of the apparatus of the invention.

Referring to FIGS. 1 through 3, it is seen that cam member 32 is of sufficient inside diameter that it does not contact shaft 20 and, consequently, does not revolve. Cam bearing member 32 is held by two pins 50 each of which pass through sleeves 52 which connect it to a collar 54. Collar 54 is, in turn, pivotally connected by anchoring bar 56 to anchor stud 58.

An operating rod 60 extends from the opposite side of collar, the outer end 62 of rod 60 being positioned for engagement with a cover-operated push rod 64. Intermediate between end 62 and collar 54 is a bearing post 66 comprising a guide slot 68 in which rod 60 is adapted for vertical movement. Positioned beneath slot 68, and normally biased between the floor 70 of turret section 16 and rod 60 is a biasing means such as spring 72.

Operation of the illustrated apparatus is as follows:

With cover 80 open, push rod 64 is in its release position and, consequently, spring 72 is expanded to lift operating rod 60. (In the illustrated embodiment of the invention operating rod 60 really is part of a clevis incorporating collar 54.) Operating rod 60, in turn, raises collar 54 and cam-bearing member 32.

Cam member 32 comprises, on the top surface thereof, two roughly semicircular, saddles 84 formed by indentations positioned 180 angular degrees apart. The followers are urged, by the force exerted by the expanding spring 72, into saddle-like indentations 84.

In the center of each saddle 84 is an indentation, or slot, 73 adapted to receive and prevent turning of the cam followers 22. (Not shown in FIG. 3 but best seen in FIGS. 1 and 2.) They are so held when the cam member 32 is pushed upwardly by spring 72 as will be the case when cover 80 is opened as described above.

A microscope slide 78 is placed in the apparatus. The raised end 48 of the slide rests on rack 26. The other end of the slide rests on a sloped surface 76 of the slide-support in bottom of waste-receiving means 28 and bears against a raised stop member 75 of waste-receiving means 28. As best seen in FIG. 3, rack 46 is able to contact slide 78 through either of two holes in bottom of waste-receiving means 28 and through holes in carrier plate 21.

After the slide is placed in the apparatus, rack 46 is lowered by manipulation of lever arm 38, a specimen of blood is dropped on the slide and the cover 80 is closed. Closing of cover 80 depresses push rod 64, causes operating rod 60 to move downwardly compressing spring 72 and allowing cam-bearing member 32 to drop clear of slide carrying assembly 18, thereby freeing cam follower members 22 for rotation. Thereupon, motor 14 is actuated to spin the blood-bearing slide 78. As the slide spins, the blood is distributed uniformly over the surface thereof. Waste blood is thrown off into waste receiving means 28 which advantageously comprises a sponge or other such absorbant waste-receiving material 29. When the motor is shut off, the slide is slowed to a random stop. The braking means is not shown in the drawings, because it is any of those well known to be suitable in the art, and forms no innovative part of the apparatus. However, it does not provide a positive braking action in the sense of stopping the slide in a single position.

When the slide bearing assembly slows to a stop, the operator lifts cover 80, thereby allowing spring 72 to move up operating rod 60 and push rod 64. Rod 60, in turn, forces cam member 32 up against cam follower rollers 22, thereby forcing rollers into a position of alignment slots 73.

Figure 5:
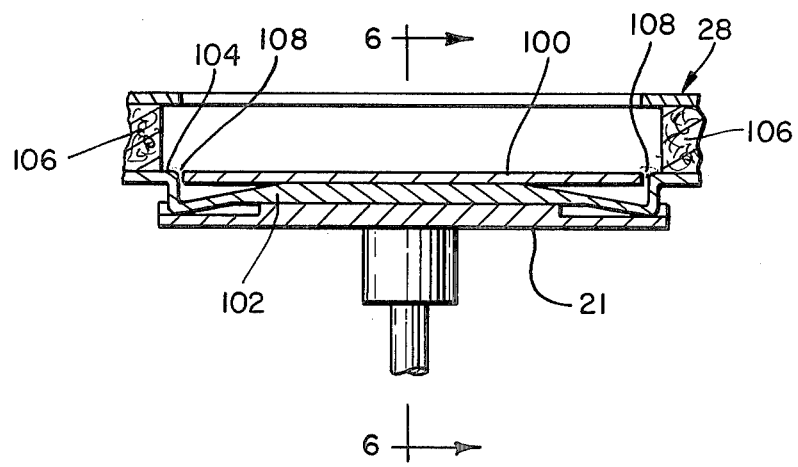
FIG. 5 is a detailed, somewhat schematic, view of a glass slide mounted according to the invention.
Figure 6:
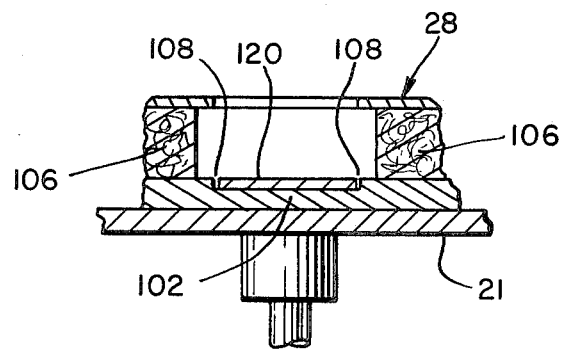
FIG. 6 is a view similar to that of FIG. 5, taken at a 90°-degree angle thereto.

FIG. 5 illustrates a slide 100 mounted on bottom of waste receiving means 28. This slide is closely positioned along each perimeter thereof, by a deck, or transition surface, 104. Surface 104 is less than 0.025 inch from the surface of the slide as shown at 108. Surface 104 is vertically positioned less than 0.005 inch from the horizontal plane of the top surface of the slide. Surface 104, when so positioned forms means to receive waste blood leaving the surface of the slide and to transmit it to the waste-receiving means, usually a porous absorbant material, 106.

It is stressed that it is intended to cover the apparatus of the invention, whether or not it exists in nonassembled parts, wherein some intrinsic or extrinsic system is so related to such parts that the system facilitates the collection of the parts for assembly at a particular place or places. Such a system could include co-ordinated shipping instructions, a co-ordinated parts-packaging systems assembly instructions or any other system which facilitates assembly of apparatus into a functioning system as defined in claims explicitly relating to assembled systems.

It is to be understood that the following claims are intended to cover all of the generic and specific features of the invention herein described and all statements of the scope of the invention which might be said to fall therebetween.

What is claimed is:

1. In a process for centrifugal distribution of liquid physiological specimens over a display surface wherein specimen waste which is spun off the display surface during said centrifugal distribution is captured by a waste-receiving means mounted proximate to and adapted to rotate with said display surface, the improvement comprising the steps of
    a. placing said display surface in a well surrounded by a smooth deck which is spaced up to about 0.025 inch from said specimen display surface, and which is vertically displaced from the plane of said display surface by less than about 0.005 inch and
    b. spinning said display surface, causing said specimen waste to leave said display surface, and to be conveyed on said deck into said waste-receiving means, said deck serving to maintain the structural integrity of said waste during its transit between display surface and waste-receiving means.
2. A process as defined in claim 1 wherein said liquid-waste tends to form elongate, fiber shaped masses when tensile stress is applied thereto.

* * * * *